(12) United States Patent
Tsuji

(10) Patent No.: US 7,222,408 B2
(45) Date of Patent: May 29, 2007

(54) STRUCTURE OF GAS SENSOR ENSURING HIGH DEGREE OF GAS-TIGHT SEAL

(75) Inventor: Nobuyuki Tsuji, Okazaki (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/913,408

(22) Filed: Aug. 9, 2004

(65) Prior Publication Data

US 2005/0028581 A1    Feb. 10, 2005

(30) Foreign Application Priority Data

Aug. 8, 2003    (JP) .............................. 2003-290153

(51) Int. Cl.
*G01N 7/00* (2006.01)
(52) U.S. Cl. ........................ 29/595; 73/31.05
(58) Field of Classification Search ............... 73/31.05; 204/428, 424, 427
See application file for complete search history.

(56) References Cited

U.S. PATENT DOCUMENTS

| | | | | |
|---|---|---|---|---|
| 4,127,464 A * | 11/1978 | Ichikawa et al. | ........... | 204/410 |
| 5,423,972 A * | 6/1995 | Mann et al. | ................. | 204/424 |
| 6,303,013 B1 | 10/2001 | Watanabe et al. | ........... | 204/428 |
| 6,415,647 B1 | 7/2002 | Yamada et al. | ............ | 73/31.05 |
| 6,446,489 B2 * | 9/2002 | Asai et al. | ................. | 73/31.05 |
| 6,513,363 B2 * | 2/2003 | Asai et al. | ................. | 73/31.05 |
| 6,585,872 B2 * | 7/2003 | Donelon et al. | ............ | 204/428 |
| 6,658,918 B2 * | 12/2003 | Hibino et al. | ............... | 73/31.05 |
| 2001/0004843 A1 * | 6/2001 | Asai et al. | ................. | 73/31.05 |
| 2001/0035045 A1 * | 11/2001 | Hibino et al. | ............... | 73/31.05 |
| 2002/0144538 A1 * | 10/2002 | Yamada et al. | ............ | 73/31.05 |
| 2003/0116435 A1 * | 6/2003 | Satou et al. | ................ | 204/424 |

FOREIGN PATENT DOCUMENTS

JP        2000-258384        9/2000

OTHER PUBLICATIONS

Chinese Official Action dated Apr. 6, 2006 issued in foreign counterpart Chinese Application 200410056288.0 and Chinese Agent cover letter.

\* cited by examiner

*Primary Examiner*—Hezron Williams
*Assistant Examiner*—Tamiko Bellamy
(74) *Attorney, Agent, or Firm*—Nixon & Vanderhye PC

(57) ABSTRACT

An improved structure of a gas sensor is provided which is designed for achieving desired crimping of an end portion of a sensor housing to establish a higher degree of gas-tight seal between the housing and a sensor element. The sensor element is fitted within the sensor housing. The end portion of the sensor housing is crimped or bent to urge the sensor element into constant abutment with an inner wall of the housing through a sealing member. The housing has an unique shape and dimensions selected to ensure the higher degree of gas-tight seal regardless of the degree of wear of a crimper and/or dimensional error of the housing.

5 Claims, 6 Drawing Sheets

STRUCTURE OF GAS SENSOR ENSURING HIGH DEGREE OF GAS-TIGHT SEAL

BACKGROUND OF THE INVENTION

1. Technical Field of the Invention

The present invention relates generally to a gas sensor which is installed, for example, in an exhaust system of automotive internal combustion engines to measure a specified component of exhaust emissions, and more particularly to an improved structure of such a gas sensor which is designed to ensure desired crimping of a sensor housing to establish a higher degree of gas-tight seal between the housing and a sensor element.

2. Background Art

Typical gas sensors installed in an exhaust system (e.g., an exhaust manifold or exhaust pipe) of automotive internal combustion engines are constructed to have a sensor element fitted hermetically within a hollow cylindrical housing. Such fitting is achieved by crimping or bending an open end portion of the housing to bring the sensor element into constant abutment with an inner wall of the housing. The sensor element has formed therein an inner chamber used as a reference gas chamber into which air is admitted as a reference gas. An outer and an inner electrode are affixed to an outer and inner wall of the sensor element. The inner electrode is exposed to the inner chamber of the sensor element, while the outer electrode is exposed to a measurement gas chamber defined around the sensor element to measure the concentration of a specified component of exhaust gas of the engine flowing into the measurement gas chamber. The crimping of the open end portion of the housing also establishes a gas-tight seal between the sensor element and the housing, that is, between the measurement gas chamber and the reference gas chamber.

U.S. Pat. No. 6,303,013 B1 to Watanabe et al., assigned to the same assignee as that of this application, teaches installation of a sensor element within a housing using the crimping techniques, as described above. The housing, as disclosed in Watanabe et al., is constructed to have an annular extension to be crimped. The annular extension has a wall tapering toward an open end of the housing and dimensions selected to avoid bulging of the annular extension after being crimped.

The tapered wall of the annular extension has a maximum thickness which is more than twice a minimum thickness thereof. Specifically, the annular extension has greatly varying thickness, thus resulting in a difficulty in deforming the annular extension uniformly. Particularly, use of a greatly worn crimper or dimensional errors in the annular extension results in a difficulty to bend the annular extension to 90°, which usually leads to a lack of adhesion between the housing and the sensor element, that is, gas-tight seal between the measurement gas chamber and the reference gas chamber.

SUMMARY OF THE INVENTION

It is therefore a principal object of the invention to avoid the disadvantages of the prior art.

It is another object of the invention to provide an improved structure of a gas sensor which is designed to achieve desired crimping of a housing in order to ensure a higher degree of gas-tight seal between a measurement gas chamber and a reference gas chamber defined within the gas sensor.

According to one aspect of the invention, there is provided an improved structure of a gas sensor working to measure a given component content in a gas. The gas sensor comprises: (a) a hollow cylindrical housing having a length with a first and a second end portion opposed to each other; (b) a sensor element fitted within the hollow cylindrical housing, the sensor element having formed therein a reference gas chamber; (c) a measurement gas-exposed cover joined to the first end portion of the hollow cylindrical housing, the measurement gas-exposed cover having defined therein a measurement gas chamber into which a gas to be measured by the sensor element is admitted and to which the sensor element is exposed; (d) a reference gas-exposed cover joined to the second end portion of the hollow cylindrical housing, the reference gas-exposed cover having defined therein a reference gas chamber into which a reference gas is admitted and which leads to the reference gas chamber of the sensor element; (e) a sealing member disposed between the first end portion of the hollow cylindrical housing and the sensor element; and (f) an annular end portion formed at the first end portion of the hollow cylindrical housing. The annular end portion includes an annular neck and an annular extension which extends from the annular neck toward a tip end of the first end portion and is greater in outer diameter than the annular neck. The annular extension is crimped to urge the sensor element into constant abutment with the hollow cylindrical housing through the sealing member to establish a gas-tight seal between the reference gas chamber of the reference gas-exposed cover and the measurement gas chamber. The annular extension before being crimped has a shape including an annular tapered portion having an outer diameter decreasing toward the tip end of the first end portion and an annular straight portion extending straight from the annular tapered portion toward the tip end of the first end portion. The annular straight portion is bent inwardly of the hollow cylindrical housing to urge the sensor element into constant abutment with the hollow cylindrical housing.

The above structure of the housing allows the straight portion to be bent to approximately 90° with a uniform degree of deformation thereof. This causes the sealing member to be pressed tightly in a longitudinal direction of the housing, thereby establishing tight adhesion between the sensor element and the housing. This ensures a higher degree of the gas-tight seal between the reference gas chamber of the reference gas-exposed cover and the measurement gas chamber. The uniform degree of deformation of the straight portion is achieved even when a many time-used crimper that is worn greatly or the annular end portion of the housing has dimensional errors.

In the preferred mode of the invention, if a thickness of a tip portion of the straight portion of the annular extension is defined as $t1$, a maximum thickness of the annular tapered portion is defined as $t3$, and a thickness of the annular neck is defined as $t4$ in the annular end portion of the hollow cylindrical housing before the annular extension is crimped, a relation of $t1<t4<t3$ may be met.

Specifically, when the thickness $t1$ is smaller than the thickness $t4$, it allows the straight portion to be deformed with little deformation of the annular neck. When the thickness $t4$ is smaller than the thickness $t3$, it facilitates ease of buckling the annular neck.

If a thickness of a base portion continuing the annular tapered portion is defined as $t2$ in the annular end portion of the hollow cylindrical housing before the annular extension is crimped, a relation of (t1+t2)/2<t4 may be met. This avoid bulging of the annular neck after the annular straight portion is crimped.

A relation of t1≦t2≦1.1×t1 may also be met. This allows the annular straight portion to have the outer diameter uniform in the longitudinal direction of the housing or to be tapered toward the tip thereof. This facilitates ease of crimping the annular straight portion.

If a length of the annular extension oriented to a longitudinal direction of the hollow cylindrical housing is defined as L1, and a length of the straight portion oriented to the longitudinal direction of the hollow cylindrical housing is defined as L2, a relation of 0.4×L1<L2<0.7×L1 may be met. This facilitates ease of crimping the annular straight portion.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 2:
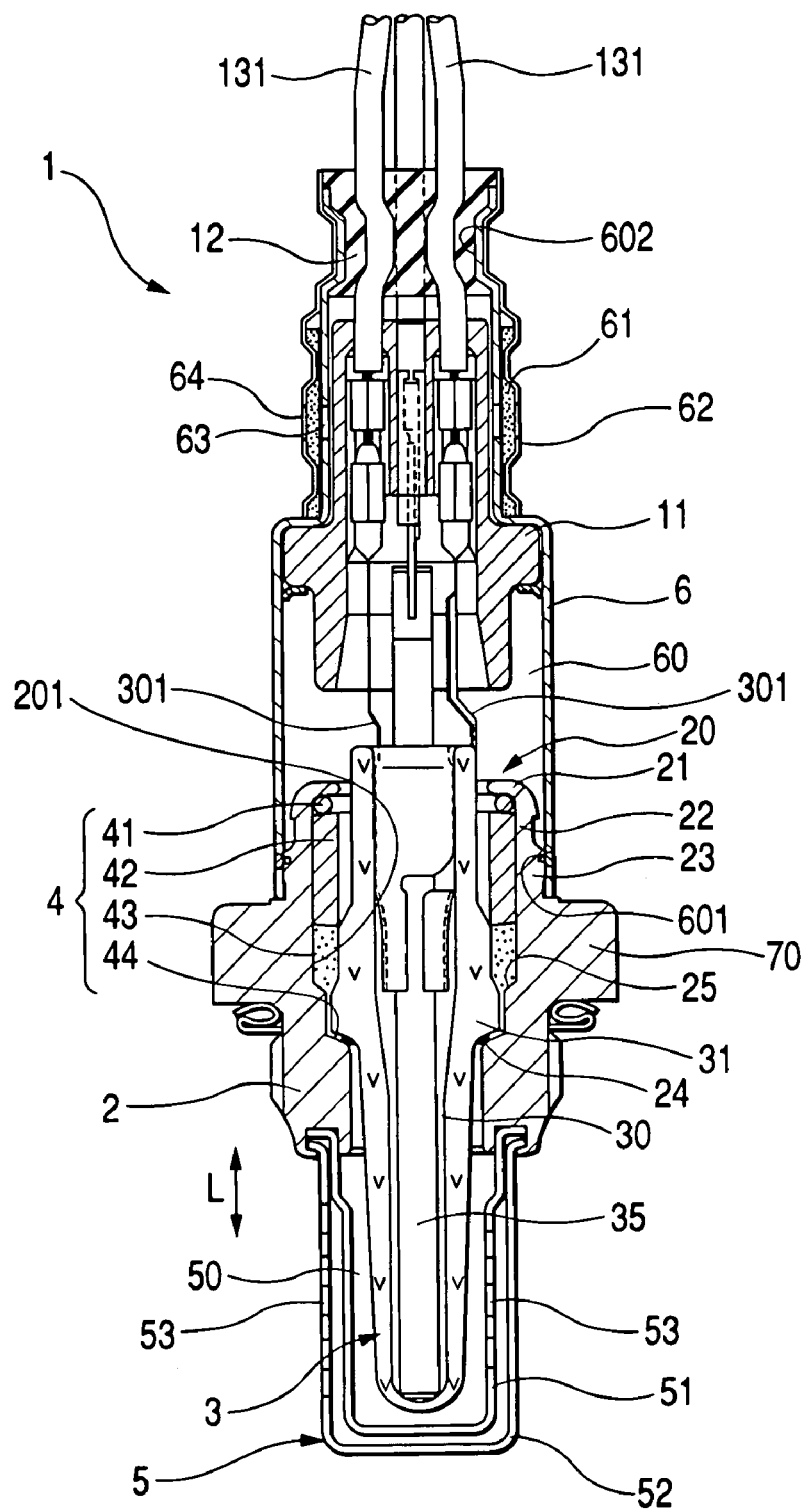
FIG. 2 is a longitudinal sectional view which shows an internal structure of a gas sensor according to the invention.

Referring to the drawings, wherein like reference numbers refer to like parts in several views, particularly to FIG. 2, there is shown a gas sensor 1 according to the invention which is designed to be installed in an exhaust system of an automotive internal combustion engine to measure an oxygen content in exhaust gasses for burning control of the engine. Note that the present invention is not limited to an oxygen sensor and may alternatively be used with a variety of gas sensors such as HC, CO, and NOx sensors.

The gas sensor 1 generally includes a sensing element 3, a hollow cylindrical housing 2, a measurement gas-exposed cover assembly 5, and an air-exposed cover 6. The housing 2 has formed therein an inner chamber 201 which is open at upper and lower ends, as viewed in the drawing. The sensor element 3 is retained within the inner chamber 201 of the housing 2. The measurement gas-exposed cover assembly 5 is joined at an end thereof to the lower end of the housing 2. The air-exposed cover 6 is joined to the upper end of the housing 2. The measure gas cover assembly 5, the housing 2, and the air-exposed cover 6 are aligned in a longitudinal direction L to define a length of the gas sensor 1.

The sensing element 3 is made of a cup-shaped solid electrolyte body which defines therein a reference gas chamber 30 into which air is admitted as a reference gas. The measurement gas-exposed cover assembly 5 has defined therein a gas chamber 50 within which a top portion (i.e., a sensing portion) of the sensor element 3 is exposed to gas to be measured. The air-exposed cover 6 has defined therein a reference gas chamber 60 leading to the reference gas chamber 30 of the sensor element 3.

Figure 1:
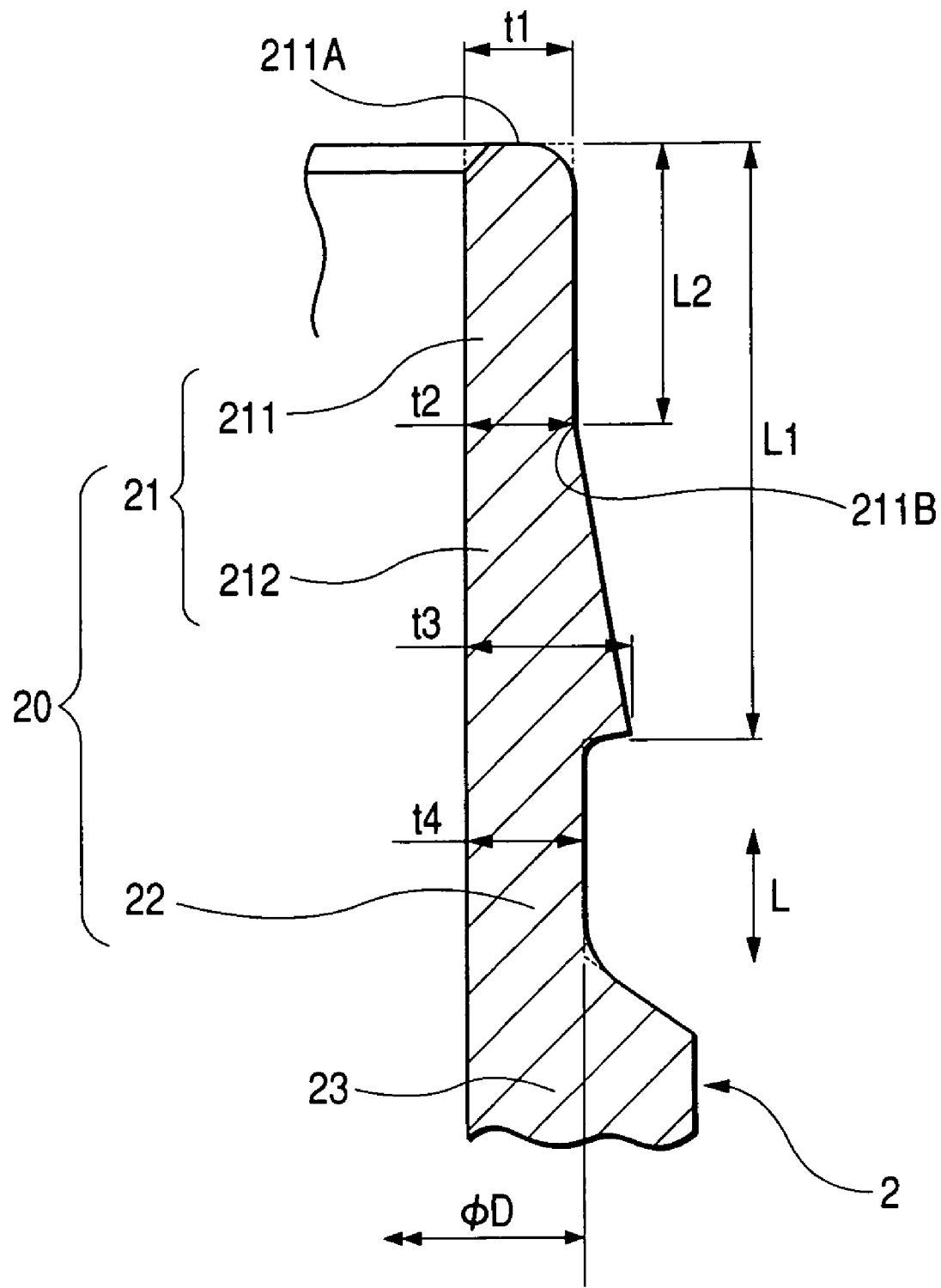
FIG. 1 is a partially enlarged longitudinal sectional view which shows a structure of a housing of a gas sensor according to the invention.

The housing 2 has an annular end portion 20 formed at the upper end thereof. The annular end portion 20 is crimped or curled inwardly of the housing 2 to retain the sensor element 1 within the housing 2 firmly. FIG. 1 is an enlarged sectional view which shows the annular end portion 20 before being curled inwardly. Sealing parts 4 are disposed between the annular end portion 20 and the sensor element 3. The firm installation of the sensor element 3 in the housing 2 is achieved by pressing and bending the annular end portion 20 inwardly in abutment with the sealing parts 4 to secure the sensor element 3 within the housing 2.

The annular end portion 20, as clearly shown in FIG. 2, is made up of an annular neck 22 and an annular crimp extension 21 continuing from the annular neck 22 to have a tip end 211A.

Before being bent to achieve the above crimp installation, the crimp extension 21 is, as clearly shown in FIG. 1, made up of an annular tapered section 212 and an annular straight section 211. The tapered section 212 has an outer wall tapering toward the tip end 211A. The straight section 211 is substantially uniform in diameter and continues from the tapered section 212. The crimp installation is, as can be seen from FIGS. 2 and 7, achieved by bending or plastic-deforming the straight section 211 inwardly to fit the sensor element 3 within the housing 2 firmly.

The gas sensor 1, as referred to herein, is an oxygen ($O_2$) sensor which is installed in the exhaust system of the automotive internal combustion engine for use in burning control thereof.

The sensor element 2 is, as described above, of a cup-shape which includes a solid electrolyte body having the reference gas chamber 30 formed therein. The operation and structure of the sensor element 2 are well known in the art and not a major part of this invention, and explanation thereof in detail will be omitted here.

The sensor element 2 has a length extending in the longitudinal direction L and has a closed top end. The solid electrolyte body has an outer and an inner electrode affixed to an outer and an inner wall thereof. Within the reference gas chamber 30, a bar-shaped heater 35 is disposed which works to heat the solid electrolyte body of the sensor element 3 up to a desired activation temperature at which the concentration of oxygen can be measured correctly.

The outer and inner electrodes of the sensor element 3 are electrically connected to sensor output lines 301. The sensor output lines 301 are electrically joined to leads 131 within a porcelain insulator 11. The leads 131 extend outside the gas sensor 1 through a bush 12.

The sealing parts 4 are, as clearly shown in FIG. 2, a powder seal 43 made of talc etc., an insulator 42, a metal ring 41, and a metal gasket 44. The insulator 42 works to insulate the sensor element 3 from the housing 2. The metal ring 41 is disposed between the annular crimp extension 21 and the insulator 42 in abutment therewith to achieve a hermetical seal therebetween. The metal gasket 44 is disposed between an outer annular tapered shoulder 31 of the sensor element 3 and an inner annular tapered shoulder 24 of the housing 2 to enhance adhesion therebetween. The powder seal 43, the insulator 42, and the metal ring 41 are disposed within a cylindrical chamber 25 defined between an outer periphery of the sensor element 2 and an inner periphery of the housing 2.

Specifically, the metal gasket 44, the tapered shoulder 31 of the sensor element 3, the powder seal 43, the insulator 42, and the metal ring 44 are retained in firm abutment with each other between the tapered shoulder 24 of the housing 2 and the crimp extension 21 of the annular end portion 20 of the housing 2 under an elastic pressure produced by crimping the extension 21 inwardly of the housing 2.

The air-exposed cover 6 is welded at an open end portion 601 thereof to the housing 2 and surrounds the annular end portion 20 of the housing 2 and is exposed to air during use of the gas sensor 1. The porcelain insulator 11 is disposed within the air-exposed cover 6. The rubber bush 12 is fitted in an open end portion 602 of the air-exposed cover 6 which is opposed to the open end portion 601 in the longitudinal direction L.

The air-exposed cover 6 has formed therein air vents 63 which lead to the reference gas chamber 60 for inducting the air thereinto as the reference gas. A cylindrical water-repellent filter 61 is disposed around the air vents 63. An outer cover 62 is affixed to a small-diameter portion of the air-exposed cover 6. Such affixing is achieved by crimping the outer cover 62, thereby also retaining the filter 61 between the outer cover 62 and the air-exposed cover 6. The outer cover 62 also has air vents 64 communicating with the air vent 63 through the filter 61.

The air as used as the reference gas in the sensor element 3 enters the air vents 63 and 64 from outside the gas sensor 1 and flows into the reference gas chamber 30 in the sensor element 3 through the reference gas chamber 60 in the air-exposed cover 6.

The measurement gas-exposed cover assembly 5 is, as described above, installed at an end thereof in an annular groove formed in the bottom of the housing 2. The measurement gas-exposed cover assembly 5 is made up of an inner cover 51 and an outer cover 52 both of which have gas inlets 53 through which the measurement gas is admitted into the gas chamber 50 to which the sensing element 3 is exposed.

The housing 2 has, as shown in FIGS. 1 and 2, a cover weld portion 23 to which the air-exposed cover 6 is welded. The cover weld portion 23 is disposed within the open end portion 601 of the air-exposed cover 6. The cover weld portion 23 has an outer diameter smaller than a maximum outer diameter of the housing 2. The cover weld portion 23 is formed between the annular end portion 20 and a flange 70 of the housing 2.

The straight section 211 of the crimp extension 21 is, as described above, substantially uniform in diameter. Similarly, the cover weld portion 23 is substantially uniform in diameter.

The crimping of the annular crimp extension 21 is accomplished with cold crimping and hot crimping. The cold crimping is achieved by pressing the annular straight section 211 vertically (i.e., in the longitudinal direction L) to bend it using a cold crimper at a room temperature. The hold crimping is achieved after the cold crimping by placing a hot crimper in abutment with the bent annular straight section 211, heating and softening the annular straight section, and pressing the annular straight section 211 to deform it further. We have evaluated a crimping condition, as will be discussed below, of the annular crimp extension 21 after being bent by the cold crimping.

Figure 7:
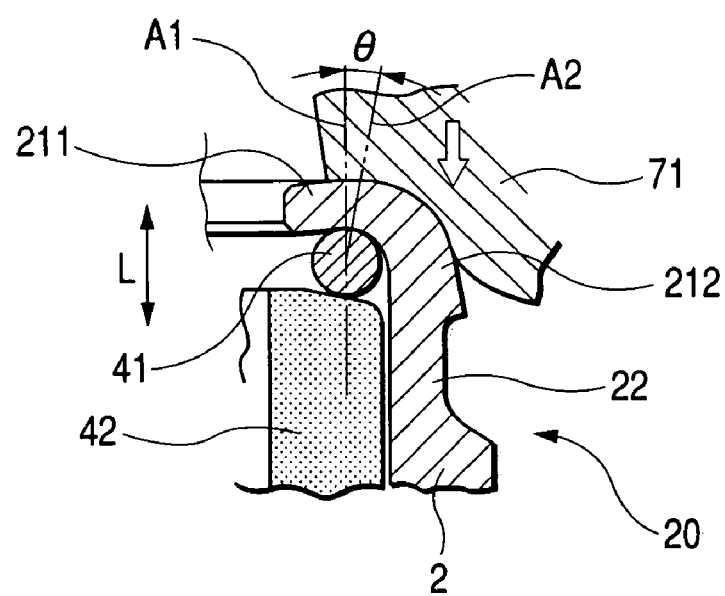
FIG. 7 is a partially enlarged longitudinal sectional view which shows a structure of the end portion of the housing, as illustrated in FIG. 6, after being crimped.

The crimping condition is, as shown in FIG. 7, expressed by a parameter of an angle $\theta$ which a line A1 extending through the center of the metal ring 41 in the longitudinal direction L makes with a line A2 extending through the center of the metal ring 41 and a contact between an outer surface of the metal ring 41 and an inner surface of the annular straight section 211 of the annular crimp extension 21. The angle $\theta$ will also be referred to as a crimp angle below. We have concluded that more near the crimp angle $\theta$ is to zero (0°)., the more excellent the crimping condition is.

The crimp angle $\theta$ of 0° is achieved when the annular straight section 211 has been bent to approximately 90°. When the crimp angle $\theta$ of 0° is achieved, it results in a maximum pressure acting on the powder seal 43.

The shape of the annular crimp extension 21 of the housing 2 before being crimped is specially designed to enhance the degree of gas-tight sealing between the housing 2 and the sensor element 3. Specifically, the annular crimp extension 21 has dimensions t1 to t4 and L1 and L2, as discussed below.

Referring back to FIG. 1, the dimension t1 is the thickness of the tip end 211A of the annular straight section 211, that is, the distance between the inner surface of an open end portion of the straight section 211 exposed to the inner chamber 201 and the outer surface of the open end portion of the straight section 211. The dimension t2 is the thickness of a base portion 211B of the straight section 211, that is, the distance between the inner and outer surface of the annular crimp extension 21 at an interface between the straight section 211 and the tapered section 212. The dimension t3 is the maximum thickness of the tapered section 212, that is, the maximum distance between the inner surface of the tapered section 212 exposed to the inner chamber 201 and the outer surface of the tapered section 212. The dimension t4 is the thickness of the annular neck 22, that is, the distance between the inner surface of the annular neck 22 exposed to the inner chamber 201 and the outer surface of the annular neck 22.

The dimension L1 is the length of the annular crimp extension 21 in the longitudinal direction L of the housing 2, that is, the distance between the end surface of the tip end 211A and an interface between the tapered section and the annular neck 22. The dimension L2 is the length of the straight section 211, that is, the distance between the end surface of the tip end 211A and the interface between the straight section 211 and the tapered section 212.

The dimensions t1 to t4 and L1 and L2 of the annular crimp extension 21 have relations of t1<t4<t3, (t1+t2)/2<t4, t1≦t2≦1.1×t1, and 0.4×L1<L2<0.7×L1. For example, the dimensions t1 and t2 are equal to each other and are approximately 0.9 mm. The dimension t3 is approximately 1.3 mm. The dimension t4 is approximately 11.0 mm. The dimension L1 is approximately 3.7 mm. The dimension L2 is approximately 1.8 mm.

The reason for the above dimensional relations will be discussed below.

The relation of t1<t4 has been derived by the experimental fact that when the thickness t1 of the tip end 211A of the straight section 211 is smaller than the thickness t4 of the annular neck 22, it allows the straight section 211 to be bent by the cold crimping with little deformation of the annular neck 22. The relation of t4<t3 has been derived by the experimental fact that when the thickness t4 of the annular neck 22 is smaller than the maximum thickness t3 of the tapered section 212, it allows the annular neck 22 to be buckled by the hot crimping in the longitudinal direction L with little buckle of the tapered section 212 in the longitudinal direction L.

Figure 4:
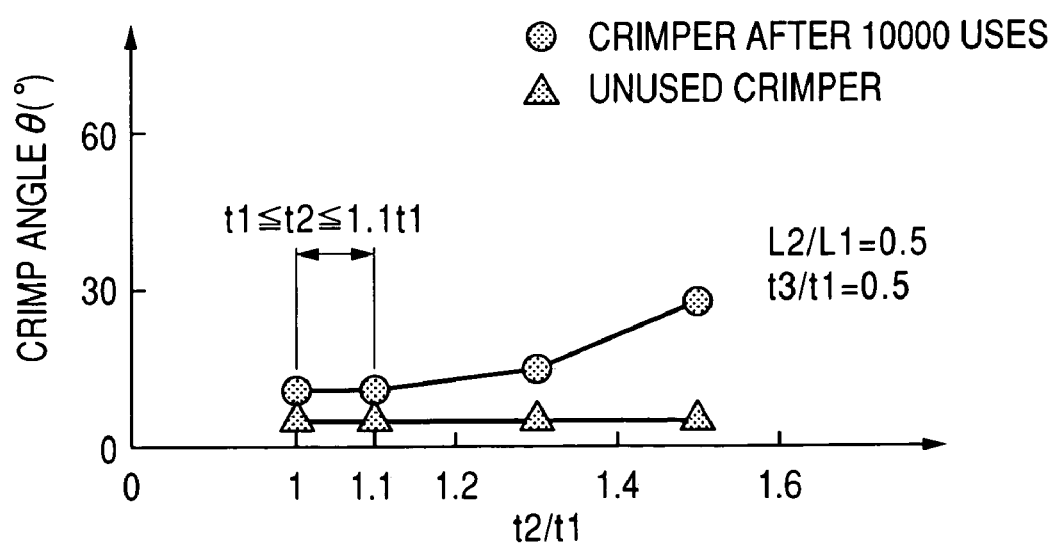
FIG. 4 is a graph which shows a crimp angle as a parameter indicating the degree of crimping of an end portion of housing samples which have different thickness relations.
Figure 5:
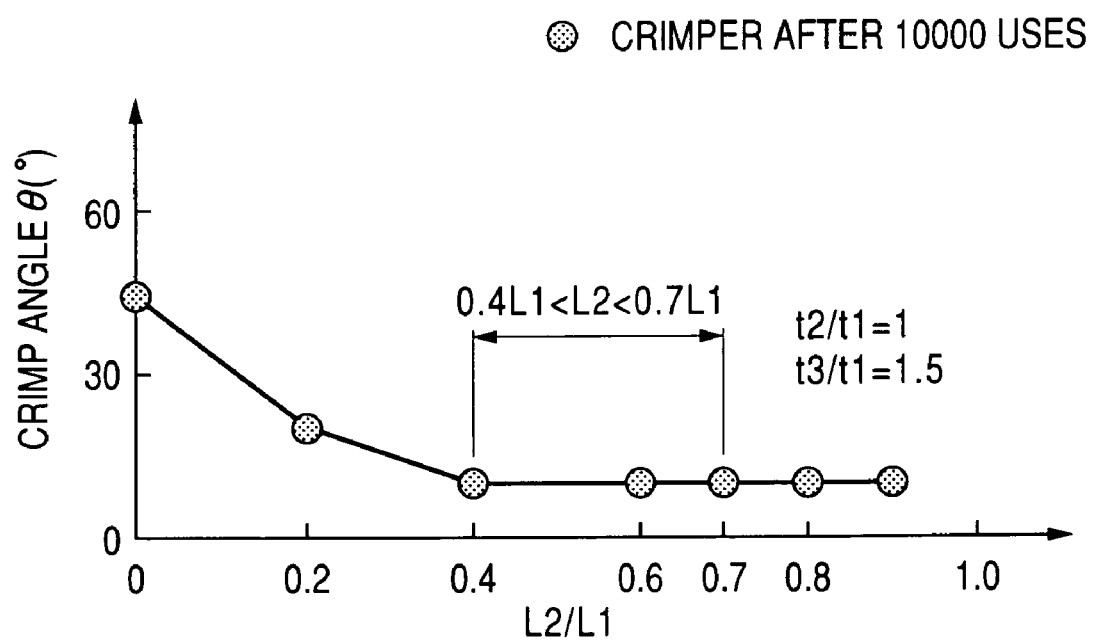
FIG. 5 is a graph which shows a crimp angle as a parameter indicating the degree of crimping of an end portion of housing samples which have different length relations.

We performed first to third tests supporting evidences for deriving the relations (t1+t2)/2<t4, t1≦t2≦1.1×t1, and 0.4×L1<L2<0.7×L1. Results of the tests are shown in FIGS. 3 to 5.

Figure 3:
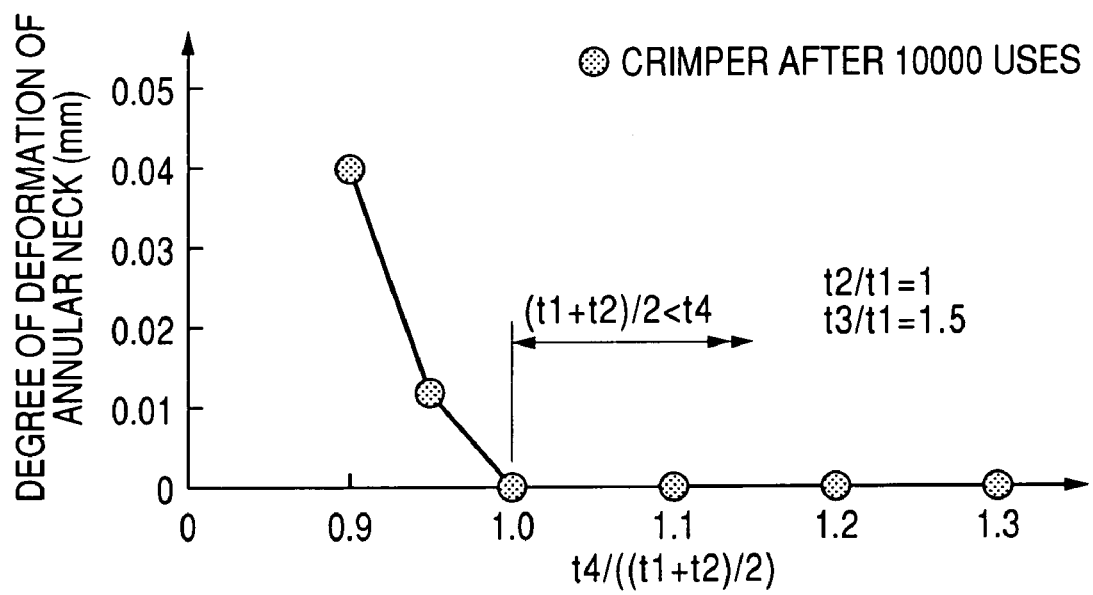
FIG. 3 is a graph which shows the degree of deformation of an annular neck of housing samples which have different thickness relations after an end portion of the housing is crimped.

FIG. 3 is a graph which represents the results of the first test as performed to derive the evidence for the relation of (t1+t2)/2<t4. The abscissa axis indicates the value of t4/((t1+t2)/2) The ordinate axis indicates a change (mm) in outer diameter ϕD of the annular neck 22 of the housing 2.

We prepared six samples of the housing 2 which had values of t4/((t1+t2)/2) between 0.9 to 1.3, subjected the samples to the cold crimping, and measured changes in outer diameters ϕD of the annular necks 22 of the samples. Note that a crimper after 10000 uses was used in the first test in view of wear thereof which usually arises after a lot of uses. Each of the samples was designed to have relations of t2/t1=1 and t3/t1=1.5.

The graph shows that when the value of t4/((t1+t2)/2) is between 1.0 to 1.3, the outer diameter ϕ D of the annular necks 22 of each of the samples hardly changes, while when the value of t4/((t1+t2)/2) is between 0.9 to 0.95, the outer diameter ϕD of the annular necks 22 of each of the samples increases. In other words, it is found that when an average thickness of the annular straight section 211 (i.e., (t1+t2)/2) is less than or equal to the thickness t4 of the annular neck 22, the outer diameter ϕD of the annular necks 22 of each of the samples hardly changes. For this reason, the housing 2 of this embodiment is designed to have the relation of (t1+t2)/2<t4.

FIG. 4 is a graph which represents the results of the second test as performed to derive the evidence for the relation of t1≦t2≦1.1×t1. The abscissa axis indicates the value of t2/t1. The ordinate axis indicates the crimp angle θ of the annular crimp extension 21, as illustrated in FIG. 7.

We prepared four samples of the housing 2 having values of t2/t1 between 0.9 to 1.3, subjected the samples to the cold crimping, and measured the crimp angle θ (°) of the annular crimp extension 21. Note that a crimper after 10000 uses was used in the second test in view of wear thereof which usually arises after a lot of uses. Each of the samples was designed to have relations of L2/L1=0.5 and t3/t1=1.5.

The graph shows that when the value of t2/t1 is 1 or 1.1, it permits the crimp angle θ of the annular crimp extension 21 to be decreased below 13°, while when the value of t2/t1 is 1.3 or 1.5, it causes the crimp angle θ to be increased above 15°. In other words, it is found that when the value of t2/t1 is between 1 and 1.1, it permits the crimp angle θ of the annular crimp extension 21 to be decreased desirably. For this reason, the housing 2 of this embodiment is designed to have the relation of t1≦t2≦1.1×t1.

We also performed an additional test using an unused crimper. Other test conditions are identical with those in the second test. Results of the test show that it is possible to decrease the crimp angle θ of the annular crimp extension 21 below approximately 6° using the unused crimper. We have also found that when the value of t2/t1 is less than 1, it causes the annular straight section 211 to increase in diameter toward the tip end 211A and the housing 2 having such a dimension is unsuitable for the cold crimping required in this embodiment.

FIG. 5 is a graph which represents the results of the third test as performed to derive the evidence for the relation of 0.4×L1<L2<0.7×L1. The abscissa axis indicates the value of L2/L1. The ordinate axis indicates the crimp angle θ of the annular crimp extension 21, as illustrated in FIG. 7.

We prepared seven samples of the housing 2 having values of L2/L1 between 0 to 0.9, subjected the samples to the cold crimping, and measured the crimp angle θ (°) of the crimp extension 21. Note that a crimper after 10000 uses was used in the second test in view of wear thereof which usually arises after a lot of uses. Each of the samples was designed to have relations of t2/t1=1 and t3/t1=1.5.

The graph shows that when the value of L2/L1 is between 0.4 and 0.9, it permits the crimp angle θ of the annular crimp extension 21 to be decreased below 10°, while when the value of L2/L1 is 0 or 0.2, it causes the crimp angle θ to be increased above 20°. In other words, it is found that when the value of L2/L1 is greater than or equal to 0.4, it permits the crimp angle θ of the annular crimp extension 21 to be decreased desirably. We have also found that when the value of L2/L1 is greater than or equal to 0.7, it results in an undesirabley increase in the length L2 of the annular straight section 211 relative to the length L1 of the annular crimp extension 21, thereby causing the hot crimping following the cold crimping to heat the annular straight section 211 up to an undesirable temperature, resulting in a difficulty in buckling the annular neck 22 desirably, which leads to a lack of stress oriented in the longitudinal direction L which is required to ensure constant adhesion between the housing 2 and the sensor element 3. For this reason, the housing 2 of this embodiment is designed to have the relation of 0.4×L1<L2<0.7×L1.

The manner in which the straight section 211 of the annular crimp extension 21 of the annular end portion 20 is bent or crimped inwardly of the housing 2 to retain the sensor element 3 within the housing 2 firmly will be discussed below.

Prior to crimping the straight section 211, the metal gasket 44 is, as shown in FIG. 2, placed on the annular tapered shoulder 24 of the housing 2, after which the sensor element 3 is inserted into the inner chamber 201 of the housing 2. Subsequently, powder such as talc is loaded into the cylindrical chamber 25 between the outer wall of the sensor element 3 and the inner wall of the housing 2 and compressed using a press to form the powder seal 43.

The insulator 43 and the metal ring 41 are placed on the powder seal 43.

Figure 6:
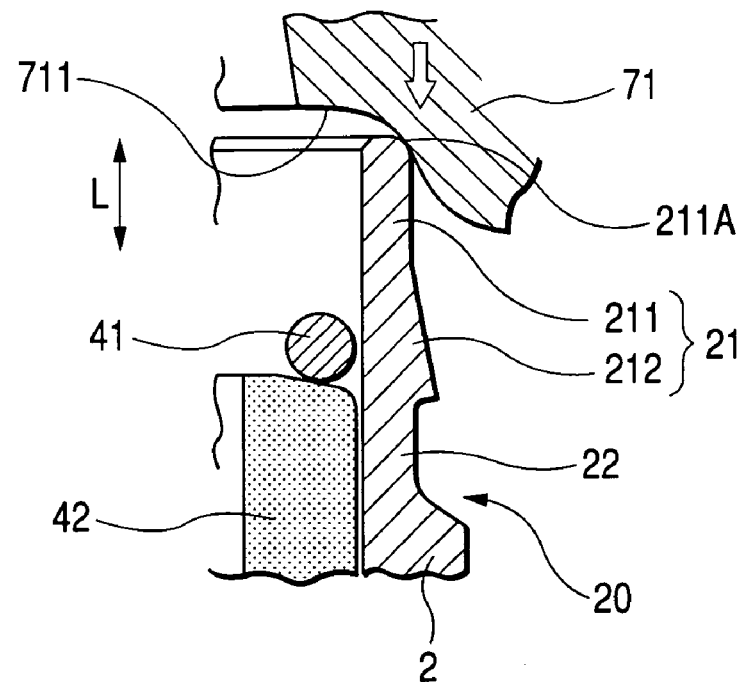
FIG. 6 is a partially enlarged longitudinal sectional view which shows a manner in which an end portion of a housing is crimped.

Next, the annular crimp extension 21 of the housing 2 is bent inwardly by two steps: the cold crimping and the hot crimping. The cold crimping is accomplished at a room temperature using a ring-shaped crimper 71, as illustrated in FIG. 6. The hot crimping is accomplished by pressing the annular crimp extension 21 and heating the annular neck 22 to soften it, thus causing the annular neck 22 to buckle.

The ring-shaped crimper 71 has an inner surface 711 curved into a shape matching with an expected outer surface of the straight section 211 after being bent by the cold crimping. After the metal gasket 44, the powder seal 43, the insulator 42, and the metal ring 41 are arrayed within the cylindrical chamber 25, the crimper 71 is brought close to the housing 2 from the longitudinal direction L until it abuts the tip end 211A of the annular straight section 211 of the annular crimp extension 21.

Next, the crimper 71 is forced downward, as viewed in FIG. 7, to press or bend the annular straight section 211 into a shape contoured to conform with the shape of the inner surface 711 of the crimper 71, thereby wrapping the metal ring 41 with the straight section 211. The bending of the straight section 211 results in slight deformation of the annular tapered section 212. The straight section 211 is, as described above, uniform in thickness, so that it undergoes substantially uniform deformation as a whole. In this way, the sensor element 3 is retained firmly within the housing 2 through the metal gasket 44, the powder seal 43, the insulator 42, and the metal ring 41.

Finally, the hot crimping is performed by supplying current to the annular end portion 20 to heat it and pressing the straight section 211 further in the longitudinal direction L using a hot crimper (not shown) into a shape contoured to conform with a shape of an inner surface of the hot crimper. This causes the annular neck 22 to buckle, thereby compressing the powder seal 43 further to enhance the adhesion or gas-tight sealing between the housing 2 and the sensor element 3 through the metal gasket 44. The cold and hot crimping causes the annular crimp extension 21 to produce a great stress acting on the sealing parts 4 in the longitudinal direction L, thereby ensuring the firm adhesion between the housing 2 and the sensor element 3.

As apparent from the above discussion, the cold crimping in this embodiment enables the straight section 211 to be crimped inwardly through the crimper 71 and subjected to substantially uniform deformation. The straight section 211 is bent to substantially 90°. The crimp angle θ of the annular crimp extension 21 is minimized. The substantially 90° bend deformation of the annular straight section 211 produces tight compression of the powder seal 43 in the longitudinal direction L, thereby establishing the firm adhesion between the housing 2 and the sensor element 3 while keeping the electrical insulation of the sensor element 3 from the housing 2. This ensures the gas-tight seal between the gas chamber 50 in the measurement gas-exposed cover assembly 5 and the reference gas chamber 60 within the sensor element 3. Specifically, when the measurement gas enters the gas chamber 50, and the air or the reference gas enters the reference gas chambers 60 and 30, the gas-tight seal between the housing 2 and the gas sensor 3 provided by the sealing parts 4 works to isolate the measurement gas from the reference gas completely regardless of a rise in temperature of the measurement gas (i.e., the exhaust gas of the engine), thus enhancing the accuracy of measuring the concentration of the measurement gas (i.e., $O_2$).

Even when the many time used cold crimper 71 is used to crimp the annular crimp extension 21 of the housing 2 or when the annular crimp extension 21 has any dimensional error, the cold and hot crimping in this embodiment enables the straight section 211 to be deformed substantially uniformly and the crimp angle θ of the straight section 211 to be kept minimized.

We have found that after the cold and hot crimping, the annular neck 22 hardly change in the outer diameter φD, and the cover weld portion 23 is also hardly deformed. It is, therefore, easy to insert the cover weld portion 23 into the open end portion 601 of the air-exposed cover 6, thus facilitating ease of assembling of the housing 2 and the air-exposed cover 6.

Figure 8:
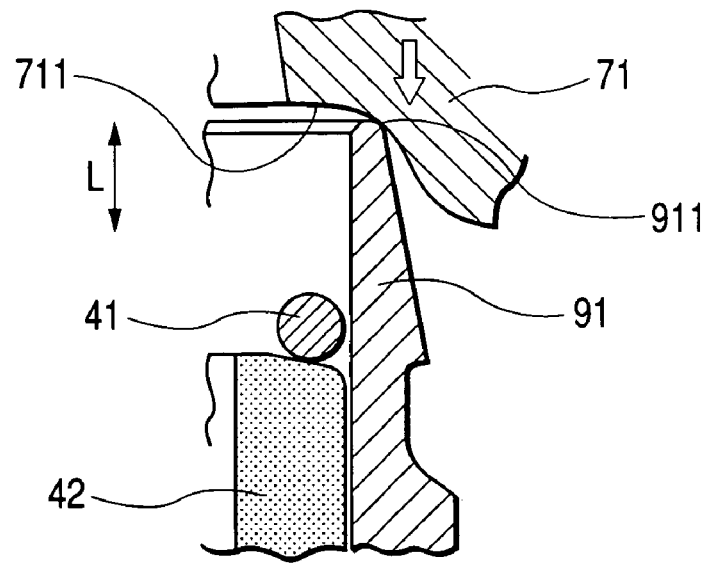
FIG. 8 is a partially enlarged longitudinal sectional view which shows a comparative example in which an end portion of a housing having a conventional structure is crimped.
Figure 9:
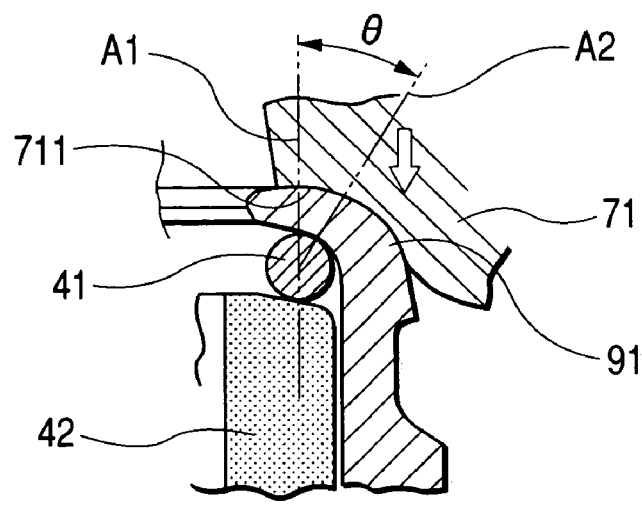
FIG. 9 is a partially enlarged longitudinal sectional view which shows a structure of the end portion of the housing, as illustrated in FIG. 8, after being crimped.

We performed a crimping test, as shown in FIG. 8, using the crimper 71 after used 10000 times to subject a crimp extension 91 of a housing, as used in a conventional gas sensor, which tapers toward an end tip 911 to the cold crimping. We found, as illustrated in FIG. 9, that it is difficult to bent the crimp extension 91 to 90° and decrease the crimp angle θ to a desired small value and that the structure of the housing 2 of the gas sensor 1 of this embodiment ensures the desired crimping of the crimp extension 21, thus establishing the higher degree of gas-tight seal between the housing 2 and the sensor element 3.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A method of manufacturing a gas sensor comprising:
providing a hollow cylindrical housing having a length with a first and a second end portion opposed to each other; a sensor element fitted within said hollow cylindrical housing, said sensor element having formed therein a reference gas chamber; a measurement gas-exposed cover joined to the second end portion of said hollow cylindrical housing, said measurement gas-exposed cover having defined therein a measurement gas chamber into which a gas to be measured by said sensor element is admitted and to which said sensor element is exposed; a reference gas-exposed cover joined to the first end portion of said hollow cylindrical housing, said reference gas-exposed cover having defined therein a reference gas chamber into which a reference gas is admitted and which leads to the reference gas chamber of said sensor element; a sealing member disposed between the first end portion of said hollow cylindrical housing and said sensor element; and an annular end portion formed at the first end portion of said hollow cylindrical housing, said annular end portion including an annular neck and an annular extension which extends from the annular neck toward a tip end of the first end portion and is greater in outer diameter than the annular neck, the annular extension having a shape including an annular tapered portion having an outer diameter decreasing toward the tip end of the first end portion and an annular straight portion extending straight from the annular tapered portion toward the tip end of said first end portion; and
crimping the annular extension so that the annular straight portion is bent inwardly of said hollow cylindrical housing.

2. A method as in claim 1, wherein if a thickness of a tip portion of the straight portion of the annular extension is defined as t1, a maximum thickness of the annular tapered portion is defined as t3, and a thickness of the annular neck is defined as t4 in the annular end portion of said hollow cylindrical housing before the annular extension is crimped, a relation of t1<t4<t3 is met.

3. A method as in claim 1, wherein if a thickness of a tip portion of the straight portion of the annular extension is defined as t1, a thickness of a base portion continuing the annular tapered portion is defined as t2, and a thickness of the annular neck is defined as t4 in the annular end portion of said hollow cylindrical housing before the annular extension is crimped, a relation of $(t1+t2)/2<t4$ is met.

4. A method as in claim 1, wherein if a thickness of a tip portion of the straight portion of the annular extension is defined as t1 and a thickness of a base portion continuing the annular tapered portion is defined as t2 in the annular end portion of said hollow cylindrical housing before the annular extension is crimped, a relation of $t1 \leqq t2 \leqq 1.1 \times t1$ is met.

5. A method as in claim 1, wherein if a length of the annular extension oriented to a longitudinal direction of said hollow cylindrical housing is defined as L1, and a length of the straight portion oriented to the longitudinal direction of said hollow cylindrical housing is defined as L2, a relation of $0.4 \times L1 < L2 < 0.7 \times L1$ is met.

* * * * *